(12) United States Patent
Vertikov et al.

(10) Patent No.: US 8,964,017 B2
(45) Date of Patent: Feb. 24, 2015

(54) OPTICAL TISSUE IMAGING BASED ON OPTICAL FREQUENCY DOMAIN IMAGING

(75) Inventors: Andrei Vertikov, Westwood, MA (US); Peter E. Norris, Cambridge, MA (US); Xiao-Li Li, Lexington, MA (US)

(73) Assignee: Tomophase, Inc., Burlington, MA (US)

( * ) Notice: Subject to any disclaimer, the term of this patent is extended or adjusted under 35 U.S.C. 154(b) by 536 days.

(21) Appl. No.: 13/392,816

(22) PCT Filed: Aug. 26, 2010

(86) PCT No.: PCT/US2010/046874
§ 371 (c)(1),
(2), (4) Date: Jul. 10, 2012

(87) PCT Pub. No.: WO2011/028628
PCT Pub. Date: Mar. 10, 2011

(65) Prior Publication Data
US 2012/0268578 A1 Oct. 25, 2012

Related U.S. Application Data

(60) Provisional application No. 61/237,284, filed on Aug. 26, 2009.

(51) Int. Cl.
*A62B 1/04* (2006.01)
*G01B 9/02* (2006.01)
(Continued)

(52) U.S. Cl.
CPC .......... *G01B 9/02057* (2013.01); *A61B 5/0066* (2013.01); *A61B 5/6852* (2013.01); *G01B 9/02004* (2013.01); *G01B 9/02064* (2013.01); *G01B 9/0205* (2013.01); *G01B 9/0209* (2013.01); *G01B 9/02091* (2013.01);
(Continued)

(58) Field of Classification Search
CPC .............. A61B 5/0066; A61B 5/6852; G01B 2290/40; G01B 2290/70; G01B 9/02004; G01B 9/0205; G01B 9/02057; G01B 9/02064; G01B 9/0209; G01B 9/02091; G02B 6/241; G02B 6/2706; G02B 6/3624
USPC .......................................................... 348/65
See application file for complete search history.

(56) References Cited

U.S. PATENT DOCUMENTS

| 4,402,311 A | 9/1983 | Hattori |
| 4,848,867 A | 7/1989 | Kajioka et al. |

(Continued)

FOREIGN PATENT DOCUMENTS

| CN | 2524241 | 12/2002 |
| EP | 0 429 297 | 5/1991 |

(Continued)

OTHER PUBLICATIONS

An, L., et al., "In vivo volumetric imaging of vascular perfusion within human retina and choroids with optical micro-angiography," Optics Express, 16(15):11438-11452, Jul. 2008.

(Continued)

*Primary Examiner* — Sath V Perungavoor
*Assistant Examiner* — Peter D Le
(74) *Attorney, Agent, or Firm* — DT Ward, PC; Donna T. Ward; Lingyun Jia

(57) ABSTRACT

Optical devices and techniques for imaging and measuring targeted objects, e.g., tissues.

2 Claims, 14 Drawing Sheets

(51) Int. Cl.
  *A61B 5/00* (2006.01)
  *G02B 6/24* (2006.01)
  *G02B 6/27* (2006.01)
  *G02B 6/36* (2006.01)

(52) U.S. Cl.
  CPC .............. *G02B6/241* (2013.01); *G02B 6/2706* (2013.01); *G02B 6/3624* (2013.01); *G01B 2290/70* (2013.01); *G01B 2290/40* (2013.01)
  USPC .......................................................... 348/65

(56) References Cited

U.S. PATENT DOCUMENTS

| | | | |
|---|---|---|---|
| 4,878,492 A | 11/1989 | Sinofsky et al. | |
| 4,991,938 A | 2/1991 | Buhrer et al. | |
| 5,088,493 A | 2/1992 | Giannini et al. | |
| 5,202,745 A | 4/1993 | Sorin et al. | |
| 5,321,501 A | 6/1994 | Swanson et al. | |
| 5,459,570 A | 10/1995 | Swanson et al. | |
| 5,659,392 A | 8/1997 | Marcus et al. | |
| 5,710,630 A | 1/1998 | Essenpreis et al. | |
| 5,784,162 A | 7/1998 | Cabib et al. | |
| 5,803,909 A | 9/1998 | Maki et al. | |
| 5,912,762 A | 6/1999 | Li et al. | |
| 6,034,774 A | 3/2000 | Marcus et al. | |
| 6,134,003 A | 10/2000 | Tearney et al. | |
| 6,201,989 B1 | 3/2001 | Whitehead et al. | |
| 6,219,565 B1 | 4/2001 | Cupp et al. | |
| 6,246,818 B1 | 6/2001 | Fukushima | |
| 6,252,666 B1 | 6/2001 | Mandella et al. | |
| 6,282,011 B1 | 8/2001 | Tearney et al. | |
| 6,377,840 B1 | 4/2002 | Gritsenko et al. | |
| 6,421,164 B2 | 7/2002 | Tearney et al. | |
| 6,451,009 B1 | 9/2002 | Dasilva et al. | |
| 6,485,413 B1 | 11/2002 | Boppart et al. | |
| 6,498,942 B1 | 12/2002 | Esenaliev et al. | |
| 6,501,551 B1 | 12/2002 | Tearney et al. | |
| 6,522,407 B2 | 2/2003 | Everett et al. | |
| 6,549,801 B1 | 4/2003 | Chen et al. | |
| 6,585,639 B1 | 7/2003 | Kotmel et al. | |
| 6,608,717 B1 | 8/2003 | Medford et al. | |
| 6,609,425 B2 | 8/2003 | Ogawa | |
| 6,615,072 B1 | 9/2003 | Izatt et al. | |
| 6,687,010 B1 | 2/2004 | Horii et al. | |
| 6,709,402 B2 | 3/2004 | Dekker | |
| 6,725,073 B1 | 4/2004 | Motamedi et al. | |
| 6,738,144 B1 | 5/2004 | Dogariu | |
| 6,753,966 B2 | 6/2004 | Von Rosenberg | |
| 6,847,453 B2 | 1/2005 | Bush | |
| 6,891,984 B2 | 5/2005 | Petersen et al. | |
| 6,901,284 B1 | 5/2005 | Maki et al. | |
| 6,903,820 B2 | 6/2005 | Wang | |
| 6,903,854 B2 | 6/2005 | Gelikonov et al. | |
| 6,943,881 B2 | 9/2005 | Wang | |
| 7,023,563 B2 | 4/2006 | Li | |
| 7,039,454 B1 | 5/2006 | Kaga et al. | |
| 7,058,155 B2 | 6/2006 | Piacsek et al. | |
| 7,170,574 B2 | 1/2007 | Tan et al. | |
| 7,207,984 B2 | 4/2007 | Farr et al. | |
| 7,254,429 B2 | 8/2007 | Schurman et al. | |
| 7,259,851 B2 | 8/2007 | Wang | |
| 7,263,394 B2 | 8/2007 | Wang | |
| 7,428,053 B2 | 9/2008 | Feldchtein et al. | |
| 7,456,965 B2 | 11/2008 | Wang | |
| 7,595,879 B2 | 9/2009 | Wang | |
| 7,706,646 B2 | 4/2010 | Wang et al. | |
| 7,831,298 B1 | 11/2010 | Wang et al. | |
| 7,970,458 B2 | 6/2011 | Norris et al. | |
| 7,999,938 B2 | 8/2011 | Wang | |
| 8,041,162 B2 | 10/2011 | Wang et al. | |
| 2002/0049370 A1 | 4/2002 | Laufer et al. | |
| 2002/0126347 A1 | 9/2002 | Hogan | |
| 2002/0131049 A1 | 9/2002 | Schmitt | |
| 2003/0020920 A1 | 1/2003 | Dave et al. | |
| 2003/0114878 A1 | 6/2003 | Diederich et al. | |
| 2003/0137669 A1 | 7/2003 | Rollins et al. | |
| 2003/0187319 A1 | 10/2003 | Kaneko et al. | |
| 2004/0001716 A1 | 1/2004 | Daou et al. | |
| 2004/0140425 A1 | 7/2004 | Iizuka et al. | |
| 2004/0218845 A1 | 11/2004 | Li et al. | |
| 2004/0246490 A1* | 12/2004 | Wang ........................... 356/479 |
| 2004/0247268 A1 | 12/2004 | Ishihara et al. | |
| 2004/0258377 A1 | 12/2004 | Berkey et al. | |
| 2004/0260158 A1 | 12/2004 | Hogan | |
| 2005/0018202 A1 | 1/2005 | Wang | |
| 2005/0053109 A1 | 3/2005 | Hogan | |
| 2005/0075547 A1 | 4/2005 | Wang | |
| 2005/0286055 A1 | 12/2005 | Wang | |
| 2006/0067620 A1* | 3/2006 | Shishkov et al. ................ 385/38 |
| 2006/0089548 A1 | 4/2006 | Hogan | |
| 2006/0100490 A1 | 5/2006 | Wang et al. | |
| 2006/0132790 A1* | 6/2006 | Gutin ........................... 356/479 |
| 2006/0204174 A1* | 9/2006 | Jones ............................. 385/37 |
| 2006/0244973 A1* | 11/2006 | Yun et al. ...................... 356/511 |
| 2007/0002327 A1* | 1/2007 | Zhou et al. ................... 356/456 |
| 2007/0063914 A1* | 3/2007 | Becker ........................... 343/840 |
| 2007/0115476 A1 | 5/2007 | Feldchtein et al. | |
| 2007/0278389 A1* | 12/2007 | Ajgaonkar et al. ........... 250/221 |
| 2008/0033300 A1 | 2/2008 | Hoang et al. | |
| 2008/0119701 A1 | 5/2008 | Milner et al. | |
| 2009/0073444 A1 | 3/2009 | Wang | |
| 2010/0091282 A1 | 4/2010 | Wang | |
| 2011/0029049 A1 | 2/2011 | Vertikov et al. | |
| 2011/0063616 A1 | 3/2011 | Wang | |
| 2011/0066035 A1 | 3/2011 | Norris et al. | |
| 2011/0285996 A1 | 11/2011 | Wang et al. | |
| 2012/0033911 A1 | 2/2012 | Wang et al. | |
| 2012/0268578 A1* | 10/2012 | Vertikov et al. ................. 348/65 |

FOREIGN PATENT DOCUMENTS

| | | |
|---|---|---|
| EP | 0 527 050 | 2/1993 |
| JP | 2001-066245 | 3/2001 |
| JP | 2002-013907 | 1/2002 |
| JP | 2004-317437 | 11/2004 |
| WO | 03/062802 | 7/2003 |
| WO | 2006/041997 | 4/2006 |
| WO | 2008/134449 | 11/2008 |

OTHER PUBLICATIONS

El-Tonsy, M.H., et al., "Continuous-wave Nd:Yag laser hyperthermia: a successful modality in treatment of basal cell carcinoma," Dermatology Online Journal, 10(2):12 pages, Oct. 2004.

European Search Report dated Nov. 18, 2010 for European Patent Application No. 05813935.3, filed Oct. 20, 2005 (9 pages).

European Search Report dated Nov. 2, 2010 for European Patent Application No. 04754292.3, filed Jun. 4, 2004 (4 pages).

Goldberg, S.N., et al., "Thermal ablation therapy for focal malignancy: a unified approach to underlying principles, techniques, and diagnostic imaging guidance," AJR American Journal Roentgenology, 174(2):323-331, Feb. 2000.

Handbook of Optics, 2nd Edition, vol. 1: Fundamentals, Techniques, & Design, Optical Society of America, McGraw-Hill Professional, pp. 42.68-42.73, Sep. 1994.

International Preliminary Report on Patentability dated Dec. 22, 2005 for International Application No. PCT/US04/17649, filed Jun. 4, 2004 (7 pages).

International Preliminary Report on Patentability dated Feb. 24, 2009 for International Application No. PCT/US05/35951, filed Oct. 5, 2005 (9 pages).

International Preliminary Report on Patentability dated Nov. 5, 2009 for International Application No. PCT/US2008/061451, filed Apr. 24, 2008 (6 pages).

International Search Report and Written Opinion dated Apr. 28, 2011 for International Application No. PCT/US2010/046874, filed Aug. 26, 2010 (6 pages).

International Search Report and Written Opinion dated Aug. 29, 2008 for International Application No. PCT/US05/35951, filed Oct. 5, 2005 (10 pages).

(56) References Cited

OTHER PUBLICATIONS

International Search Report and Written Opinion dated Nov. 20, 2009 for International Application No. PCT/US2009/035773, filed Mar. 2, 2009 (7 pages).

International Search Report and Written Opinion dated Oct. 17, 2008 for International Application No. PCT/US2008/061451, filed Apr. 24, 2008 (7 pages).

International Search Report and Written Opinion dated Oct. 4, 2007 for International Application No. PCT/US05/37730, filed Oct. 20, 2005 (5 pages).

James, A., et al., "Airway smooth muscle in health and disease; methods of measurement and relation to function," The European Respiratory Journal, 15(4):782-789, Apr. 2000.

Lucroy, M.D., et al., "Selective laser-induced hyperthermia for the treatment of spontaneous tumors in dogs," Journal of X-Ray Science and Technology, 10(3-4):237-243, (2002).

Mariampillai, A., et al., "Doppler optical cardiogram gated 2D color flow imaging at 1000 fps and 4D in vivo visualization of embryonic heart at 45 fps on a swept source OCT system," Optics Express, 15(4):1627-1638, Feb. 2007.

Miller, J.D., et al., "A Prospective Feasibility Study of Bronchial Thermoplasty in the Human Airway," Chest, 127 (6):1999-2006, Jun. 2005.

Nikfarjam, M., et al., "Interstitial laser thermotherapy for liver tumours," British Journal of Surgery, 90(9):1033-1047, Sep. 2003.

Office Action dated Feb. 12, 2010 for Chinese Patent Application No. 200580043930.4 (12 pages).

Office Action dated Mar. 17, 2010 for Japanese Patent Application No. 2006-515173 (4 pages).

Office Action dated Nov. 20, 2009 for Chinese Patent Application No. 200480021343.0 (25 pages).

Office Action dated Oct. 22, 2010 for Canadian Patent Application No. 2,528,417 (3 pages).

Tearney, G., et al., "In Vivo Endoscopic Optical Biopsy with Optical Coherence Tomography," Science, 276 (5321):2037-2039, Jun. 1997.

Tumlinson, A., et al., "Endoscope-tip interferometer for ultrahigh resolution frequency domain optical coherence tomography in mouse colon," Optics Express, 14(5):1878-1887, Mar. 2006.

Vakhtin, A.B., et al., "Common-Path Interferometer for Frequency-Domain Optical Coherence Tomography," Applied Optics, 42(34):6953-6958, Dec. 2003.

Yang, V., et al., "High speed, wide velocity dynamic range Doppler optical coherence tomography (Part I): System design, signal processing, and performance," Optics Express, 11(7):794-809, Apr. 2003.

Yun, S., et al., "Comprehensive volumetric optical microscopy in vivo," Nature Medicine, 12(12):1429-1433, Nov. 2006.

Ziemann, V., et al., "Ideas for an interferometric thermometer," Nuclear Instruments and Methods in Physics Research Section A: Accelerators, Spectrometers, Detectors and Associated Equipment, 564(1):587-589, Aug. 2006.

* cited by examiner

FIG. 5A
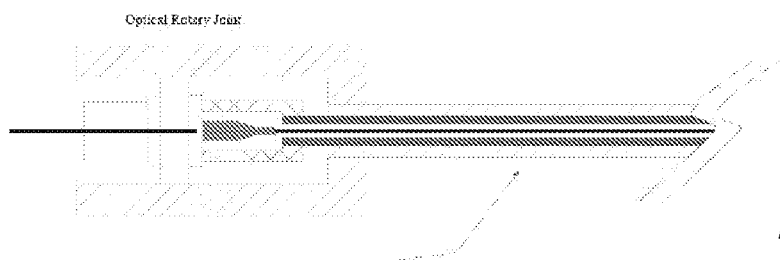
FIG. 5B
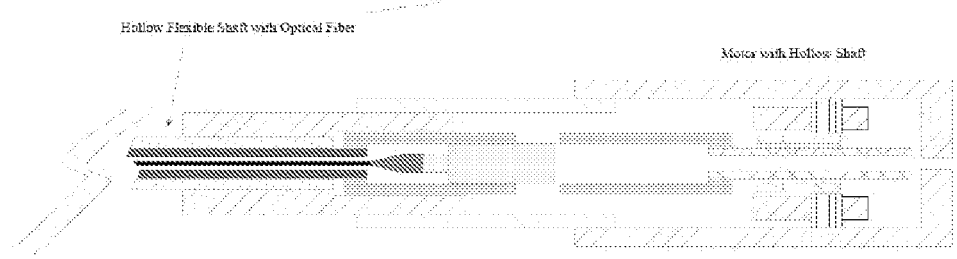
FIG. 6A
FIG. 6B
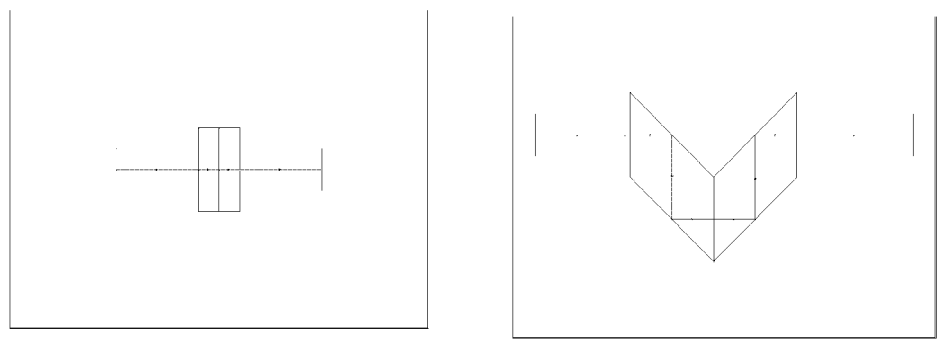

OPTICAL TISSUE IMAGING BASED ON OPTICAL FREQUENCY DOMAIN IMAGING

CROSS-REFERENCE TO RELATED APPLICATIONS

This patent application claims benefit of U.S. Provisional Application No. 61/237,284 entitled "Optical Tissue Imaging Based on Optical Frequency Domain Imaging" and filed Aug. 26, 2009. the entire disclosure of which is incorporated by reference as part of this application.

BACKGROUND

This patent document relates to optical imaging of tissues.

The need for in-vivo non-invasive cross-sectional imaging of tissue with microscopic resolution for diagnostics and image-guided therapy is well known. Optical Frequency Domain Imaging disclosed in U.S. Pat. No. 5,321,501 has been applied for such imaging.

Optical frequency domain imaging (OFDI), which may also be known as swept source optical coherence tomography uses a wavelength-swept light source to probe the amplitude, phase, polarization and spectral properties of back scattering light from the tissue. OFDI offers intrinsic signal-to-noise ratio (SNR) advantage over the time domain techniques because the interference signal can be effectively integrated through a Fourier transform enabling significant improvements in imaging speed, sensitivity and ranging depth required for in-vivo tissue imaging.

SUMMARY

This patent document includes optical devices and techniques for imaging and measuring targeted objects, e.g., tissues.

In one aspect, a device for optically imaging a sample is provided to include a swept frequency light source that produces an optical probe beam and sweeps an optical frequency of the optical probe beam in time; a waveguide to receive and guide optical probe beam in a first propagation mode and a second propagation mode different from the first propagation mode; and a disposable probe head unit removably coupled to the waveguide to receive the optical probe beam in first and second propagation modes and to reflect a first portion of the optical probe beam back to the waveguide in the first propagation mode and direct a second portion of the optical probe beam to a sample. The probe head collects reflection of the second portion from the sample and exporting to the waveguide the reflection as a reflected second portion in the second propagation mode. This device includes a mode director that directs the optical probe beam from the swept frequency light source into the waveguide and to couple light of the reflected first portion and the reflected second portion out of the waveguide without changing respective propagation modes; a mode controller coupled in an optical path of the optical probe beam between the swept frequency light source and the mode director to control light in the first and second propagation modes; a differential delay controller in an optical path of both the reflected first portion and the reflected second portion from the mode director to control a relative delay between the reflected first portion and the reflected second portion; and an optical detector unit that receives the light from the differential delay controller and to produce an electrical signal containing imaging information of the sample.

This and other aspects and their implementations are described in detail in the drawings, the description and the claims.

BRIEF DESCRIPTION OF DRAWINGS

FIGS. 5A-5B show an exemplary Drive Unit schematic including an optical rotary joint (ORJ) and a rotary drive.

FIGS. 6A-6B show exemplary achromatic ½ wavelength retarders.

DETAILED DESCRIPTION

Figure 1:
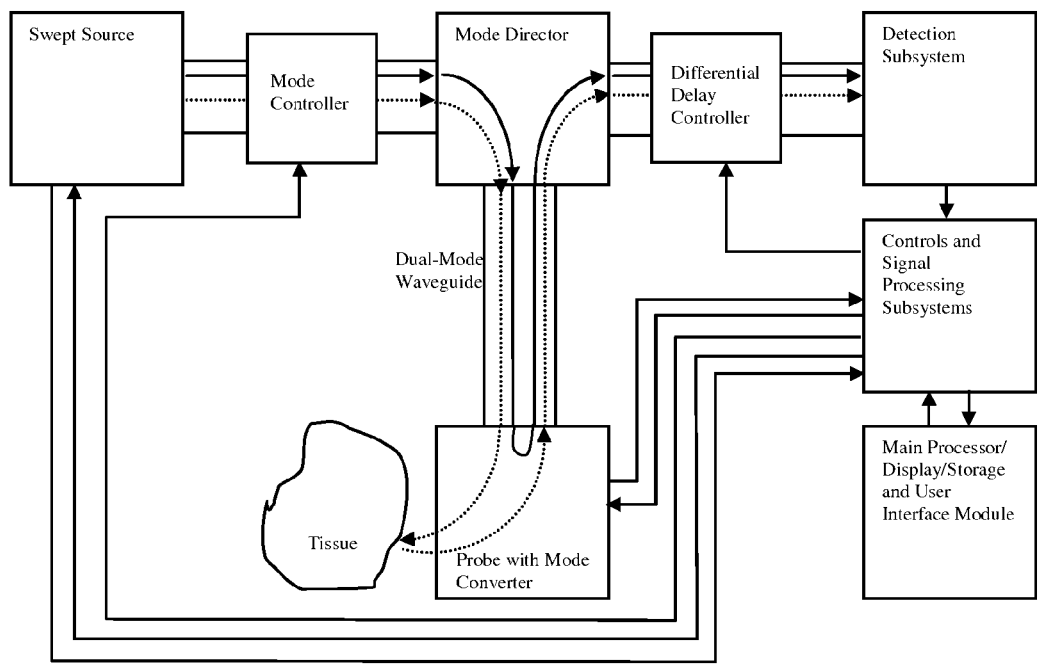
FIG. 1 shows an exemplary overall layout schematic including a probe with mode converter.

In various medical imaging applications, it is often desirable to perform the optical imaging inside tubular or other structures such as blood vessels, airways of the bronchial tree of the lungs, the gastrointestinal tract, the genital tract or the urinary tract through an endoscope in the uncontrolled environment of voluntarily and un-voluntarily motion of the endoscope and/or tissue.

Motion of endoscope and its internal component such as bending, twisting and internal fiber rotation adversely affects the sensitivity because signal and reference light will experience different polarization change. One method to mitigate this problem is to use polarization diversity detection which makes detection sub-system of imaging apparatus complicated and expensive. Thus there is a need for OFDI immune to endoscope and its component motion of as well as environmental perturbations.

Many OFDI devices use separated optical reference path and optical signal path. Clinical applications of such OFDI devices may have the difficulty of interchanging disposable parts of the catheters because the reference and the signal paths need to be accurately matched and therefore either disposable part needs to be assembled to very high tolerances or there must be means to automatically compensate for disposable length variations, further complicating the OFDI apparatus. Thus there is a need for endoscope OFDI apparatus that allows easily interchangeable disposable parts in clinical environment.

One technique to address the above issues is to use common path interferometers where the reference light is created in the distal part of the optical probe, travels the same path as the signal light and interferes with the signal light to produce an interference. U.S. Patent Publication No. US-2007-0103683-A1 entitled "Optically Measuring Substances Using Propagation Modes of Light" describes examples of optical imaging devices that use a common path interferometer and examples of tissue imaging techniques, devices and systems based on common path interferometers that maintain high sensitivity imaging and while having immunity to endoscope motion and/or environmental perturbations.

In common path interferometers, energy in light traveling in an optical path such as an optical waveguide is controlled to be in different propagation modes. Different propagation modes may be in various forms. States of optical polarization of light are examples of such propagation modes. Two independent propagation modes do not mix with one another in the absence of a coupling mechanism. As an example, two orthogonally polarization modes do not interact with each other even though the two modes propagate along the same optical path or waveguide and are spatially overlap with each other. The exemplary techniques and devices described in this application use two independent propagation modes in light in the same optical path or waveguide to measure optical properties of a sample. A probe head may be used to direct the light to the sample, either in two propagation modes or in a single propagation modes, and receive the reflected or backscattered light from the sample.

For example, optical radiation in both a first propagation mode and a second, different propagation mode can be guided through an optical waveguide towards a sample. The radiation in the first propagation mode is directed away from the sample without reaching the sample. The radiation in the second propagation mode is directed to interact with the sample to produce returned radiation from the interaction. Both the returned radiation in the second propagation mode and the radiation in the first propagation mode are coupled into the optical waveguide away from the sample. The returned radiation in the second propagation mode and the radiation in the first propagation mode from the optical waveguide are then used to extract information of the sample.

In these and other implementations based on the disclosure of this application, two independent modes are confined to travel in the same waveguides or the same optical path in free space except for the extra distance traveled by the probing light between the probe head and the sample. This feature stabilizes the relative phase, or differential optical path, between the two modes of light, even in the presence of mechanical movement of the waveguides. This is in contrast to interferometer sensing devices in which sample light and reference light travel in different optical paths. These interferometer sensing devices with separate optical paths are prone to noise caused by the variation in the differential optical path, generally complex in optical configurations, and difficult to operate and implement. The examples described below based on waveguides are in part designed to overcome these and other limitations.

The techniques, devices and systems for imaging tissues described below are based on OFDI and the optical imaging devices using common path interferometers. Examples below use different propagation modes of a waveguide for optical imaging by implementing a swept source to achieve optical imaging by using an optical mode converter and optical mode selective reflector.

FIG. 1 shows an example of such a device. The device includes a swept frequency light source that produces an optical probe beam and sweeps an optical frequency of the optical probe beam in time; a waveguide to receive and guide optical probe beam in a first propagation mode and a second propagation mode different from the first propagation mode; and a disposable probe head unit removably coupled to the waveguide to receive the optical probe beam in first and second propagation modes and to reflect a first portion of the optical probe beam back to the waveguide in the first propagation mode and direct a second portion of the optical probe beam to a sample. The probe head collects reflection of the second portion from the sample and exporting to the waveguide the reflection as a reflected second portion in the second propagation mode. This device also includes a mode director that directs the optical probe beam from the swept frequency light source into the waveguide and to couple light of the reflected first portion and the reflected second portion out of the waveguide without changing respective propagation modes; a mode controller coupled in an optical path of the optical probe beam between the swept frequency light source and the mode director to control light in the first and second propagation modes; a differential delay controller in an optical path of both the reflected first portion and the reflected second portion from the mode director to control a relative delay between the reflected first portion and the reflected second portion; and an optical detector unit that receives the light from the differential delay controller and to produce an electrical signal containing image information of the sample.

In FIG. 1, the Swept Source is a wavelength tunable coherent laser, such as for example, commercially available from, Thorlabs, Inphenix, Axsun and other laser suppliers. This Swept Source outputs wavelength tunable light, and may also output control electrical signals such as sweep trigger pulses and k-clock pulses. It may also accept control signal from user interface module and/or main processor for turning laser power on and off, perform power value adjustment and other functions. Dual Mode Waveguide formed from at least one piece of polarization maintaining (PM) fiber that supports two propagation modes with different polarization states having different propagation constants.

Figure 2A:
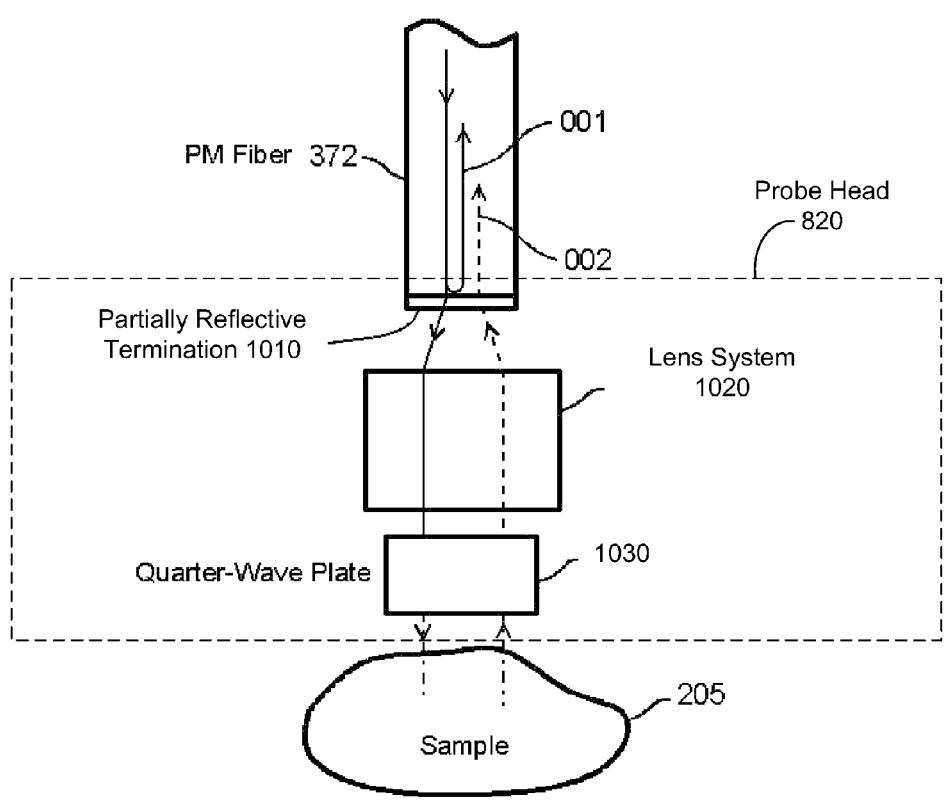
FIGS. 2A-2B show two exemplary designs for a probe head for use in sensing systems where the input light is in a single mode.
Figure 2B:
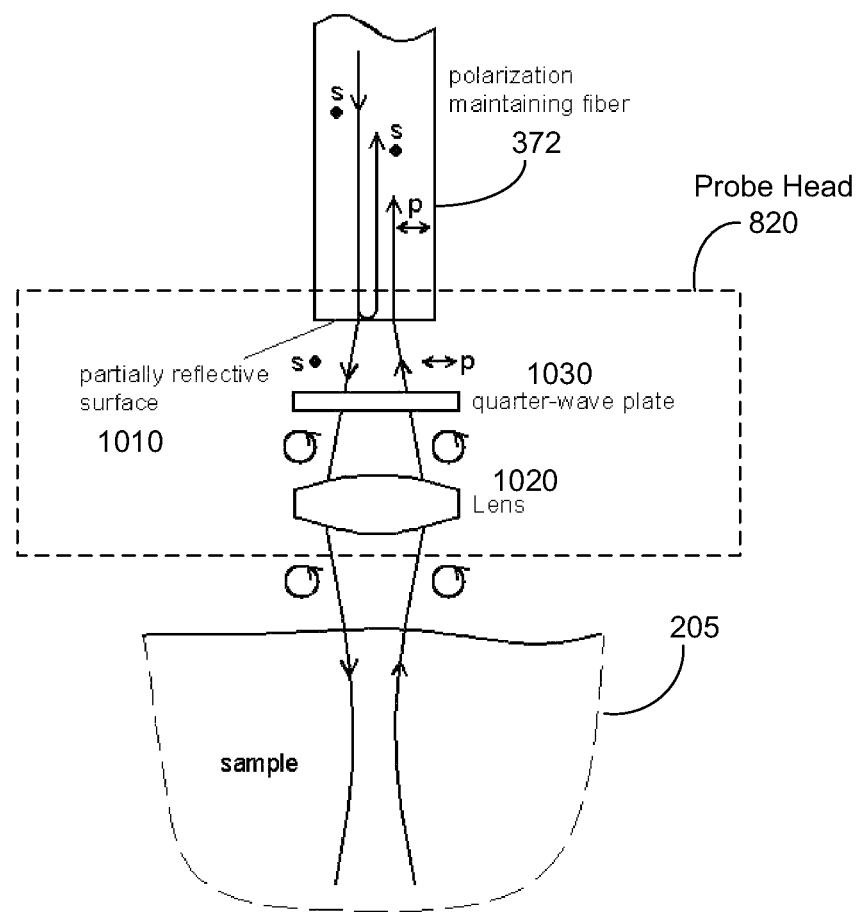

In FIG. 1, the optical probe head includes a mode converter that converts light n one mode into another mode. FIGS. 2A and 2B show two examples of the probe head 820 including a partially reflective surface 1010, a lens system 1020, and a quarter-wave plate 1030 for rotating the polarization and to convert the mode. In FIG. 2A, the termination or end facet of polarization-maintaining fiber 372 is used as the partial reflector 1010. An uncoated termination of an optical fiber reflects approximately 4% of the light energy. Coatings can be used to alter the reflectivity of the termination to a desirable value. The lens system 1020 reshapes and delivers the remaining radiation to sample 205. The other role played by the lens system 1020 is to collect the radiation reflected from the sample 205 back into the polarization-maintaining fiber 372. The quarter wave plate 1030 is oriented so that its optical axis makes a 45-degree angle with the polarization direction of the transmitted light. Reflected light from the sample 205 propagates through the quarter wave plate 1030 once again to become polarized in a direction perpendicular to mode 001, i.e. mode 002. Alternatively, the quarter wave plate 1030 may be replaced by a Faraday rotator. The head design in FIG. 2B changes the positions of the lens system 1020 and the quarter wave plate or Faraday rotator 1030.

Figure 3:
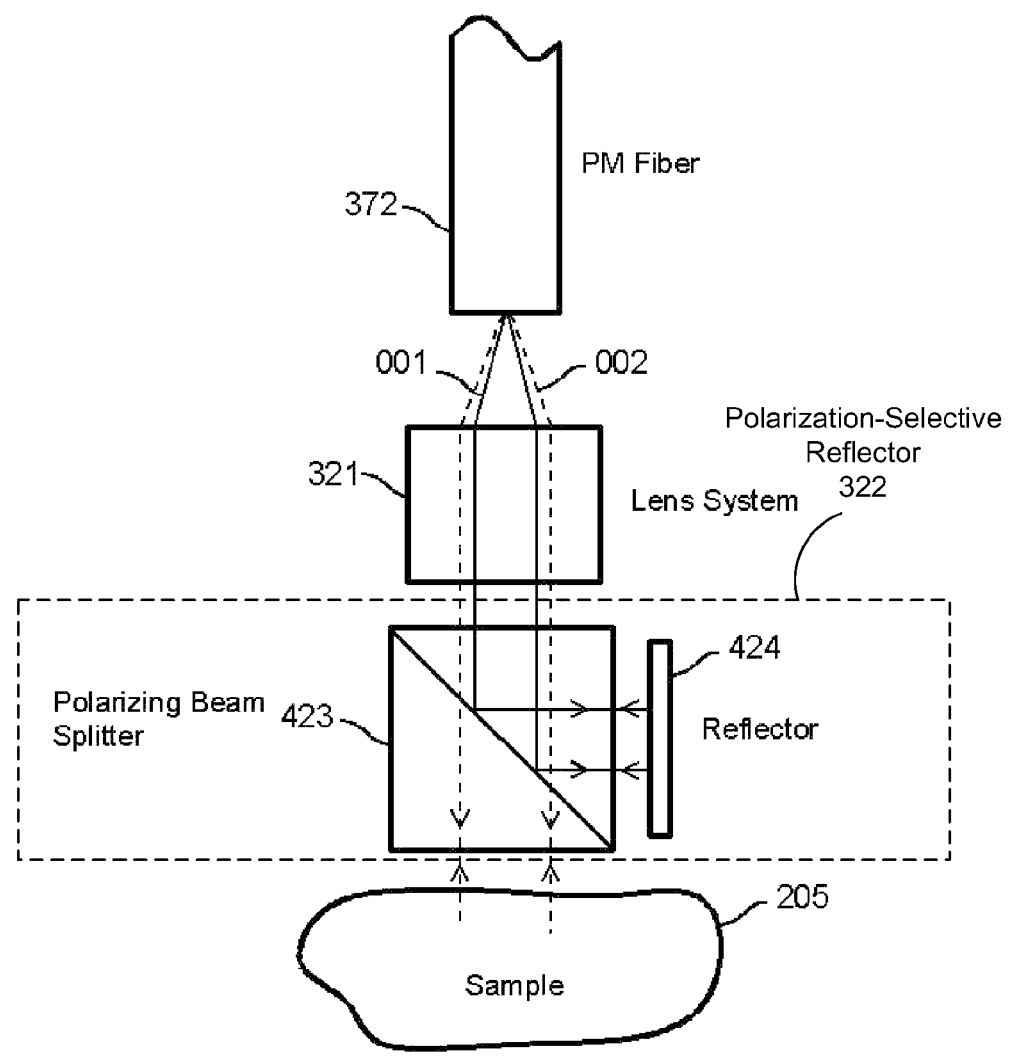
FIG. 3 shows an exemplary implementation of a probe head and a polarization-selective reflector (PSR).

The above design of incorporating a mode converter in the optical head may be replaced by designs using mode-selective reflectors. FIG. 3 shows details of the probe head 320 and an example of the polarization-selective reflector (PSR) 322. The PSR 322 includes a polarizing beam splitter (PBS) 423 and a reflector or mirror 424 in a configuration as illustrated where the PBS 423 transmits the selected mode (e.g., mode 002) to the sample 205 and reflects and diverts the other mode (e.g., mode 001) away from the sample 205 and to the reflector 424. By retro reflection of the reflector 424, the reflected mode 001 is directed back to the PBS 423 and the lens system 321. The reflector 424 may be a reflective coating on one side of beam splitter 423. The reflector 424 should be aligned to allow the reflected radiation to re-enter the polarization-maintaining fiber 372. The transmitted light in the mode 002 impinges the sample 205 and the light reflected and back scattered by the sample 205 in the mode 002 transmits through the PBS 423 to the lens system 321. The lens system 321 couples the light in both the modes 001 and 002 into the fiber 372.

In implementations, the PSR design can be used to control the ratio of light power going to the sample by controlling the power ratio between the two propagation modes using the Mode Controller. It is also understood that this embodiment includes configuration when only one mode is selectively partially reflected from distal termination, and partially transmitted to the tissue. In this case no separate mode mixing is required in Detection Subsystem and non-polarizing beam-splitters can be used for balanced detection.

Figure 4:
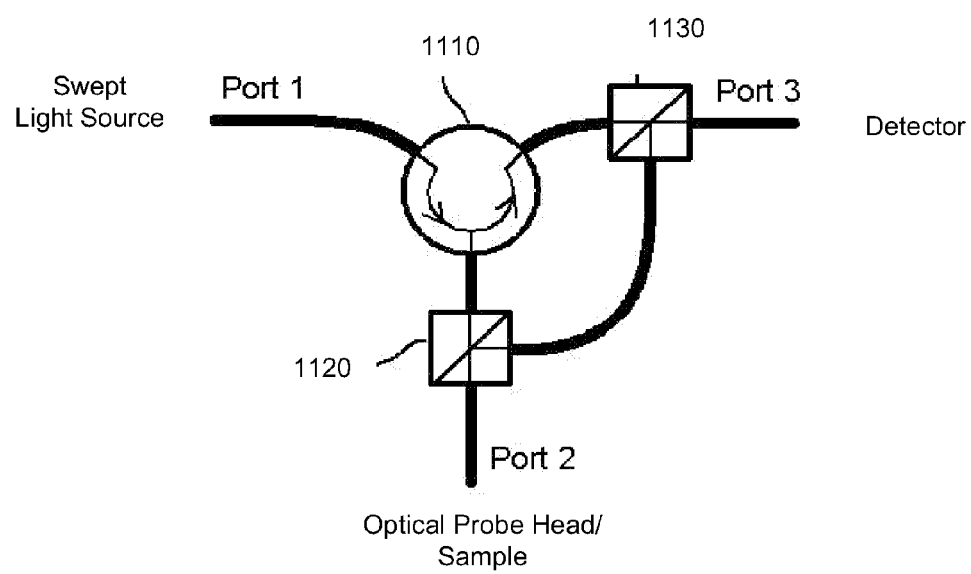
FIG. 4 shows an exemplary light director that includes a polarization-maintaining optical circulator and two polarization beam splitters.

The Mode Director in FIG. 1 can be a polarization insensitive circulator. FIG. 4 shows an example for such a mode director which is a polarization preserving circulator and includes a polarization-maintaining optical circulator 1110 and two polarization beam splitters 1120 and 1130. The polarization-maintaining circulator 1110 is used to convey only one polarization mode among its three ports, rather than both modes as in the case shown in FIGS. 3, 5A and 5B. The polarizing beam splitter 1120 and 1130 are coupled to polarization-maintaining circulator 1110 so that both polarization modes entering Port 2 are conveyed to Port 3 and remain independent.

The Mode Controller can be disposed between the swept source and the mode director and may be implemented in various configurations, including commercially available inline polarization controllers. The mode controller allows dynamic control of amplitude and phase relationship between two propagation modes. Such controllers can be commercially available, e.g., the Model PCD-M02-B product from General Photonics. The mode controller can also be disposed between the Mode Director and the probe head and/or between the Mode Director and the Detection Subsystem. The Mode Controller converts the source state of polarization (SOP) into required SOP and dynamically compensates source SOP drift and SOP effects of the optical rotary joints.

The device in FIG. 1 can include a probe assembly that includes a non-disposable Drive Unit and a Disposable Catheter.

The non-disposable Drive Unit is shown in FIG. 5 and includes an optical rotary joint (ORJ) and a rotary drive. ORJ is optically connected at its stator end to the Mode Director, while ORJ fiber attached to rotor having optical connector such as FC, SC, or any small form factor connector. The ORJ is mechanically connected on the rotor side to the rotary drive via a hollow flexible shaft with the optical fiber of the optical rotary joint located inside the hollow flexible shaft. The rotary drive can be a direct-drive DC or stepper motor with a hollow shaft or a hollow shaft in a single or double bearing driven via gear or belt mechanisms. The bore of the hollow shaft is large enough so that the whole Disposable Catheter can be inserted at least from one end into the rotary drive. The rotary drive has means to engage and disengage the coupling of the flexible shaft of optical rotary joint so that the Disposable Optical Probe with Mode Converter can be easily connected and disconnected. On the opposite side of the rotary drive unit there is collet-type or keyed coupling or any other coupling that transfers torque from rotary drive the internal flexible shaft of the Disposable Catheter. The rotary drive also has means to connect the outer sheath of the Disposable Catheter to the drive housing.

For operation with PM fibers, the optical rotary joint needs to maintain polarization. One type of PM optical rotary joints (ORJs) is disclosed in U.S. Pat. No. 4,848, 867 and U.S. Patent Publication No. US-2008-0267562-A1 entitled "Delivering light via optical waveguide and multi-view optical probe head," which are incorporated by reference as part of this document. The ORJ can be configured to include a rotary member, a fixed member, two optical fiber collimators and a ½ wavelength plate for coupling a PM fiber connected to the rotary member with another PM fiber connected to the fixed member, and gears for rotating the ½ wavelength plate with a speed equal to half the rotational speed of the PM fiber of the rotary member side. It is obvious for anyone skilled in the art that the ½ wavelength plate needs to be substantially achromatic in the region of the wavelength tuning of the swept source. Typically, standard zero order ½ waveplates made, for example, from quartz can be used for this purpose. The other two types of achromatic ½ wavelength retarders particular suitable for OFDI application of PM ORJ are shown in FIGS. 6A and 6B. FIG. 6A depicts compound waveplate consisting of two waveplates of different material. Various materials such as quartz and MgF2 can be used for such plates. FIG. 6B depicts the standard Fresnel rhombs that rely on total internal reflection to produce required ½ wavelength retardation.

Figure 7A:
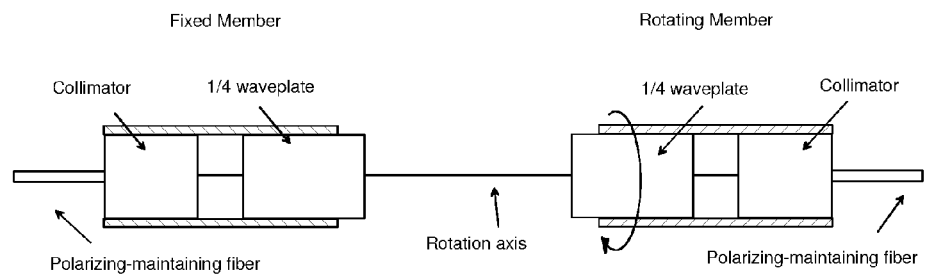
FIG. 7A depicts an exemplary polarization maintaining optical rotary joint including ¼ waveplates.

Another way to realize PM ORJ is shown in FIG. 7A, where the rotary joint comprises a rotary member, a fixed member, two optical fiber collimators and two ¼ wavelength plates for coupling a PM fiber connected to the rotary member with another PM fiber connected to the fixed member, one ¼ waveplates attached to collimator on the fixed member and aligned at 45 degrees to the axes of PM fiber of the said collimator while the other ¼ waveplate attached to the collimator on the rotary member and aligned at 45 degrees to the axes of PM fiber of the said collimator. The ¼ wavelength plates can be substantially achromatic and the retardation types described in the previous paragraph can be modified to produce ¼ wavelength retardation.

Figure 8A:
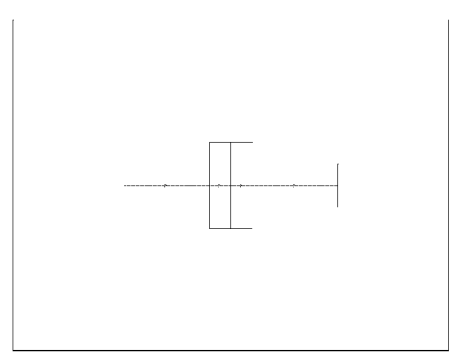
FIGS. 8A-8B show exemplary configurations for achromatic ¼ wavelength retarders.
Figure 8B:
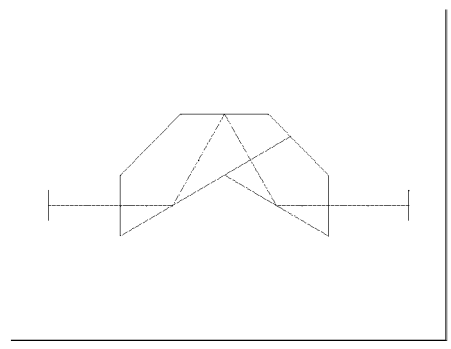

FIGS. 8A and 8B show two more possible configurations for achromatic ¼ wavelength retarders that can be used in the PM ORJ. FIG. 8A shows compound waveplate consisting of one ¼ waveplate and one ½ waveplate made of the same material with axes of the two waveplates oriented 60 degrees to each other. FIG. 8B shows achromatic ¼ waveplate using retardation of internal reflections similar to standard Fresnel rhombs but with additional reflections so that input and output beams can be made collinear facilitating compactness of the rotary joint.

Figure 7B:
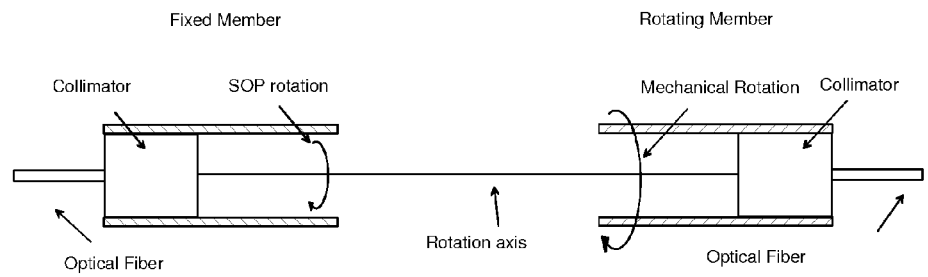
FIG. 7B depicts an exemplary optical rotary joint including dynamic state of polarization (SOP) control.

Yet another way to realize PM ORJ is shown in FIG. 7B, where the rotary joint comprises a rotary member, a fixed member, two optical fiber collimators for coupling a PM fiber connected to the rotary member with another PM or non-PM fiber connected to the fixed member. In this configuration, a dynamic polarization controller disposed anywhere between the source and the PM optical rotary joint controls SOP of the fiber connected to the static member in such way so that polarization is maintained in the rotating PM fiber.

Figure 9A:
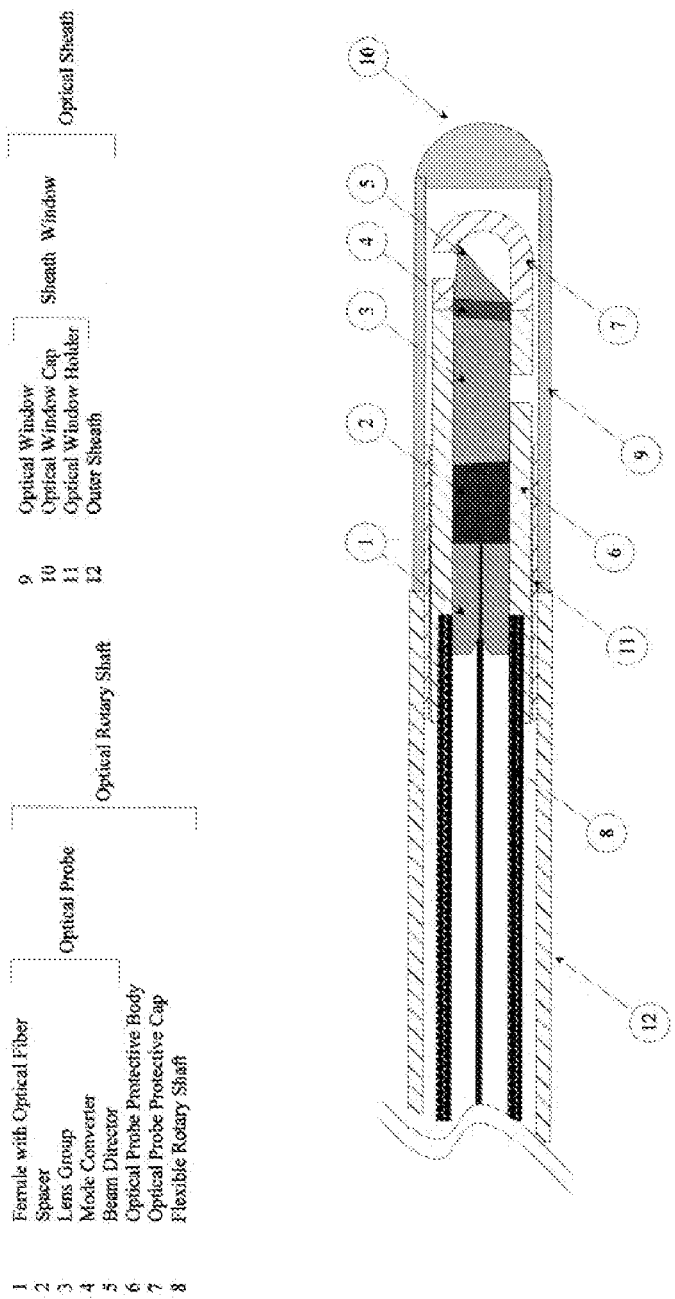
FIGS. 9A-9B show the distal end and proximal end schematics of a disposable catheter.
Figure 9B:
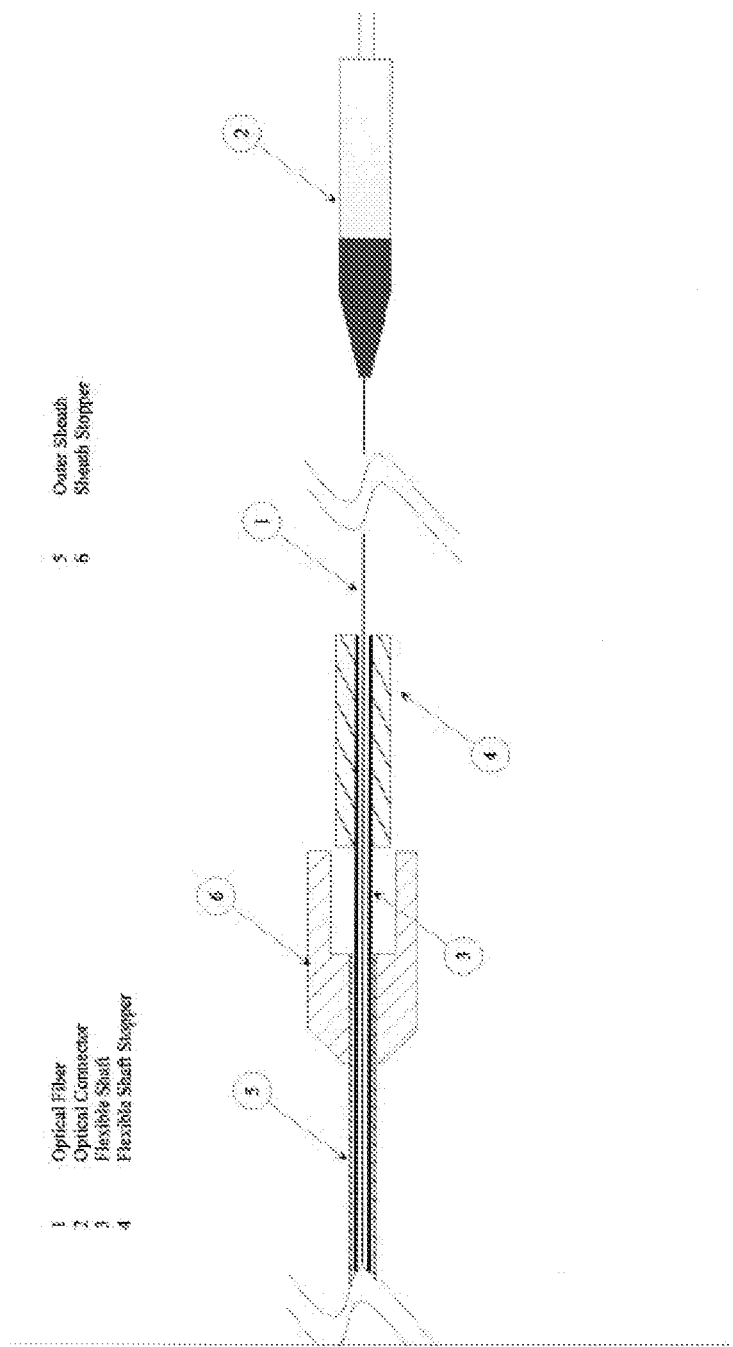

FIGS. 9A and 9B show distal end and the proximal end of the Disposable Catheter, respectively. The Disposable Catheter includes Optical Rotary Shaft inserted in the Optical Sheath. The Optical Rotary Shaft comprises Optical Probe inserted in the hollow Flexible Rotary Shaft with the Flexible Shaft Stopper on the proximal end of the Disposable Catheter. The said stopper has means to transfer torque from the Drive Unit to the said flexible shaft. On the distal end, the hollow flexible shaft may be directly attached to the optical probe by adhesive or welding process or may be attached to the Optical Probe Protective Body. The said Optical Protective Body is in turn attached to the Optical Probe. The Optical Probe Protective Body may have further Optical Probe Protective Cap to facilitate insertion of the Optical Rotary Shaft into the Optical Sheath during manufacturing.

The Optical Probe comprises PM optical fiber inserted in appropriate fiber ferrule, the said fiber having partially reflective termination at the distal end so that some fraction of light will return in the same mode from this termination. The fiber ferrule is followed by (in the direction of light propagation from fiber to the tissue) a spacer, then by a lens system that focuses the transmitted fraction of light onto the tissue and collects the back-scattered light, mode converter that converts light from one mode to the other so that collected back-scattered light propagates in different propagation mode, and light directing element that direct light at desired angles, e.g., an angle between 145 and 5 degrees relative to rotational axis of the Optical Rotary Shaft. The ferrule, the spacer, the lens system, the mode converter and the directing element can be bonded together, or at least some of the mentioned elements can be bonded together, or they can be separately attached to the Optical Probe Protective body or any other separate housing. At the proximal end, the optical fiber is terminated with a standard fiber connector, preferably small form factor connector.

The spacer is preferably a rod of high index material or, alternatively an air gap to obtain a small fraction of reflected light back from the fiber termination, e.g., 0.1-5%. The spacer has one surface angle polished to minimize back-reflections for optimal sensitivity.

The lens system can be implemented by a GRIN lens with angle polished facets to minimize back-reflection from these surfaces. It can be also other miniature standard lens with surface curvature or combination of GRIN lens and surface curvature known as C-lens, or any combination lenses.

The directing element is preferably a prism utilizing at least one internal reflection from its surfaces, such as, for example, 90 deg prism. The reflecting surface can be also coated with appropriate material to facilitate the reflection. The directing element can be also deviation prism, such as, for example, 20 degree prism. It can be also a prism comprising combination of reflective and deviating surfaces, or a combination of separate reflective and deviating surfaces.

Either a ¼ wavelength linear retarder with axes aligned 45 degrees to the linear polarization orientation at the distal end of the optical fiber or non-reciprocal polarization rotator also known as Faraday rotator can be used as a mode converter provided that they are sufficiently achromatic and compact to be used in the optical probes. It is understood that location of the mode converter is not critical for its operation, although generally the location between the lens system and the deviating element is preferred. Several examples of possible configurations of the optical probe with such mode converters are shown in FIGS. 10A-F.

Figure 10A:
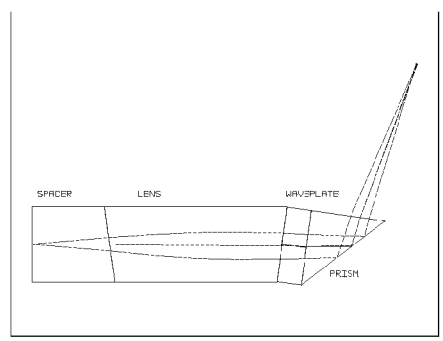
FIGS. 10A-10C show exemplary mode converter birefringent material.

FIG. 10A shows a mode converter in the form of waveplate made from birefringent material such as quartz of the appropriate thickness. The directing element relying on reflection will have its own linear retardation. For example the internal reflection of 90 degree prism of BK7 glass produces ~35 degree retardation between s and p polarizations. Therefore the said waveplate need to have retardation such that combined retardation with the deviation element is 90 degree. Alternatively, the directing element may be aligned relative to polarization state at the distal end of the optical fiber so that all reflections will be purely s or p reflection. It is understood that the said waveplate can be made of several pieces of birefringent material to make the waveplate substantially achromatic as described in the PM ORJ section of the of present invention.

Figure 10B:
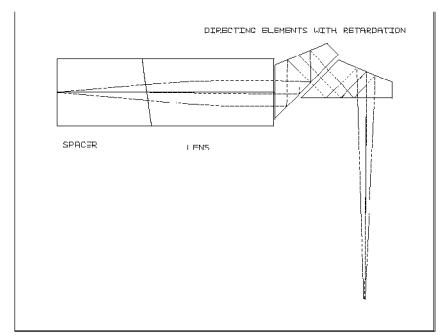

FIG. 10B shows an example of configuration where the directing element acts as a mode converter utilizing retardation effects upon internal Fresnel reflections, or reflection from coated surfaces. In this case no additional waveplate is required. With the practical selection of optical material, typically at least two reflections will be needed to acquire 90 degree retardation. It is understood that many prism configurations are possible that will have at least two reflections resulting is total 90 degree retardation.

Figure 10C:
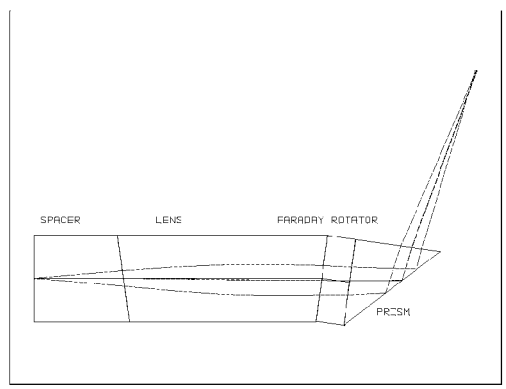

FIG. 10C shows a configuration with one 45 degree Faraday rotator as a mode converter. The location of the Faraday rotator is not critical; however location after the lens system is preferred because of better performance of such rotators with collimated light. The example of material that can be used for such rotators is MGL Garnet because it does not require external magnet resulting in compactness of the optical probe.

Figure 10D:
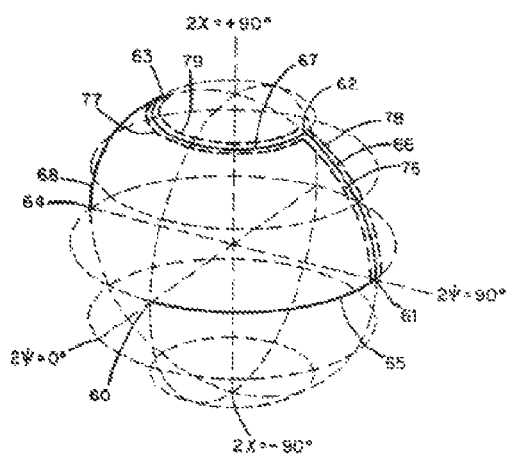
FIG. 10D shows an exemplary achromatic 45 degree polarization rotator.

The achromatic performance for such Faraday rotators in the spectral range of that the swept source is significant for OFDI. The U.S. Pat. No. 4,991,938. which is incorporated by reference as part of this document, teaches how to achieve achromatic performance for polarization rotators using combination of non-reciprocal rotators of different lengths and linear retarders. Two rotators of different lengths with the opposite rotations are used with the ratio of two lengths being equal to cos X (X is the retardation angle of each of the two waveplate oriented at 45 degrees relative to input polarization as illustrated in FIG. 10D). The '938 patent also discloses how to use prisms with internal reflections in such achromatic polarization rotators.

Figure 10E:
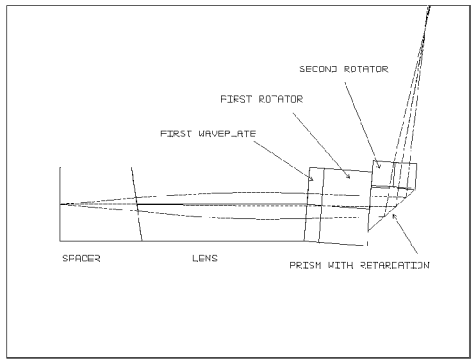
FIGS. 10E-10F show exemplary optical probes with achromatic mode converters.

FIG. 10E shows an example of optical probe with achromatic mode converter utilizing two faraday rotators and two linear retarders. In this example, the first polarization rotator is +90 degree Faraday rotator, disposed after a first linear retarder of 60 degree retardation. The said first linear retarder is 60 deg retardation waveplate oriented 45 degrees relative to the linear polarization state at the distal end of the optical fiber. The second polarization rotator is −45 degree Faraday rotator disposed after the second linear retarder of 60 degree retardation oriented the same way as the first retarder. The second retarder may be a prism with internal reflection producing 60 degree retardation or combination of a waveplate and the prism. It is understood that several more combination of two rotators and two waveplates are possible to achieve the achromatic performance of polarization rotation as disclosed in U.S. Pat. No. 4,991,938

Figure 10F:
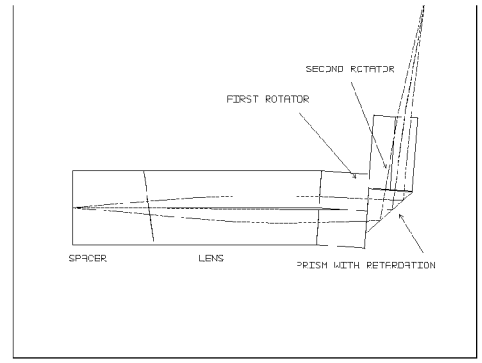

FIG. 10F shows an example of an optical probe with achromatic mode converter when the polarization rotation is not achromatic upon single pass through all the elements by the light, but achromatic upon double pass. In this case only one linear retarder is required and the directing element in the form of prism can be used as such retarder. In this example the first polarization rotator is +90 degree Faraday rotator, followed by a directing element producing approximately 48 degree retardation. There are many combinations of material and angle of incidence that can produce such retardation upon one reflection, for example, 90 degree prism made of material with refractive index approximately equal to 1.58. The second polarization rotator is −135 degree Faraday rotator. It is understood that several more combination of two rotators and one linear retarder are possible to achieve the achromatic performance of mode converter of this type.

The Optical Sheath consist of the Outer Sheath made of appropriate material and the Optical Sheath Window which can be attached to the distal end of the said sheath with adhesive or with heat shrinking or fusion process. The said window may have Optical Window Holder to facilitate the attachment process. The optical window may further have Optical Window Cap to facilitate insertion of the Disposable Catheter. It is also possible to have an integral optical element fabricated by molding that will combine the functions of optical window, cap and window holder in one integral element. The outer sheath can be made of transparent material so that the outer sheath itself acts as an optical window with no separate optical window required. The Optical sheath may also contain index matching liquid to minimize light back reflection. In this case, all the reflecting surfaces of the directing element in contact with the index matching liquid need to be either metalized or sealed to ensure proper internal reflection.

Figure 11A:
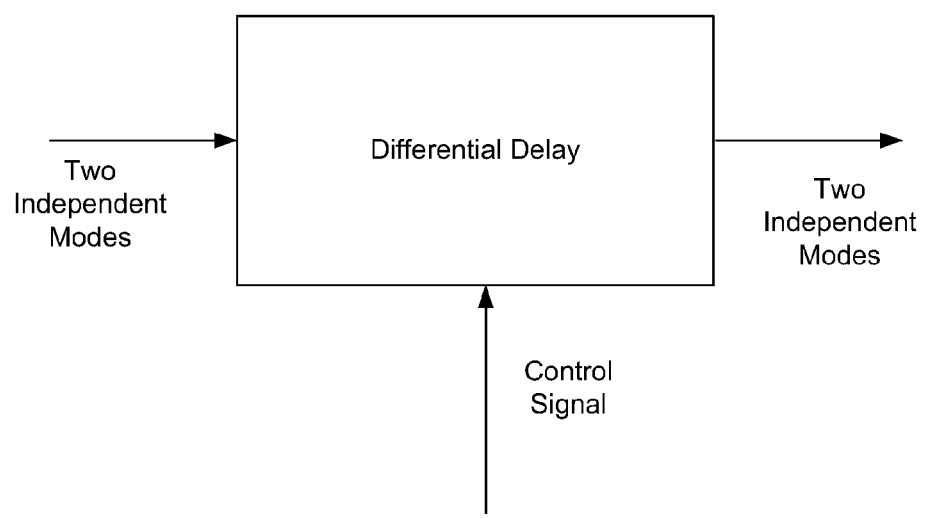
FIGS. 11A shows an exemplary optical differential delay modulator.

Differential Delay Controller in FIG. 1 changes the group delay between the two propagation modes for the optimal performance of the OFDI. A number of hardware choices are available for differential delay controller. FIG. 11A illustrates the general design of the controller where an external control signal is applied to control a differential delay element to change and modulate the relative delay in the output. Either mechanical or non-mechanical elements may be used to produce the desired relative delay between the two modes and the modulation on the delay.

In one implementation, a non-mechanical design may include one or more segments of tunable birefringent materials such as liquid crystal materials or electro-optic birefringent materials such as lithium niobate crystals in conjunction with one or more fixed birefringent materials such as quartz and rutile. The fixed birefringent material provides a fixed delay between two modes and the tunable birefringent material provides the tuning and modulation functions in the relative delay between the two modes. FIG. 11A illustrates an example of this non-mechanical design where the two modes are not physically separated and are directed through the same optical path with birefringent segments which alter the relative delay between two polarization modes.

Figure 11B:
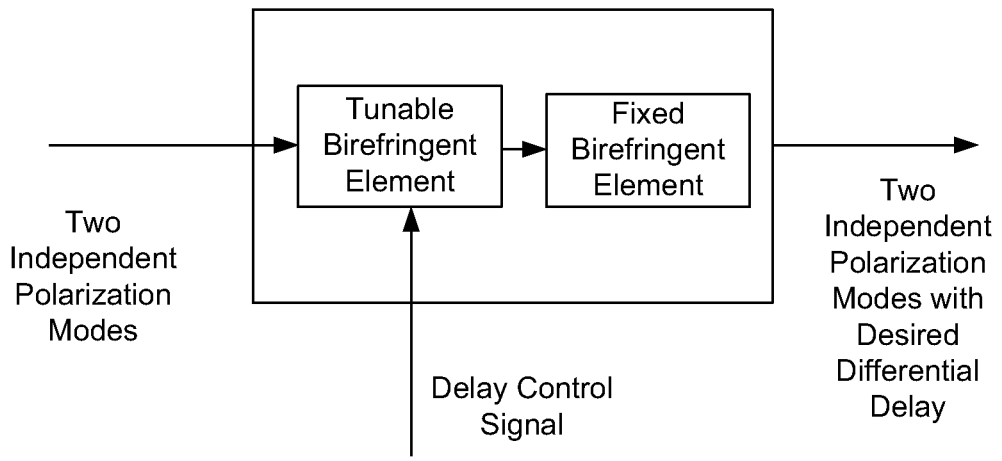
FIGS. 11B-11C show exemplary devices for implementing the optical differential delay modulator of FIG. 11A.

FIG. 11B shows a different design where the two modes in the received light are separated by a mode splitter into two different optical paths. A variable delay element is inserted in one optical path to adjust and modulate the relative delay in response to an external control signal. A mode combiner is then used to combine the two modes together in the output. The mode splitter and the mode combiner may be polarization beams splitters when two orthogonal linear polarizations are used as the two modes.

Figure 11C:
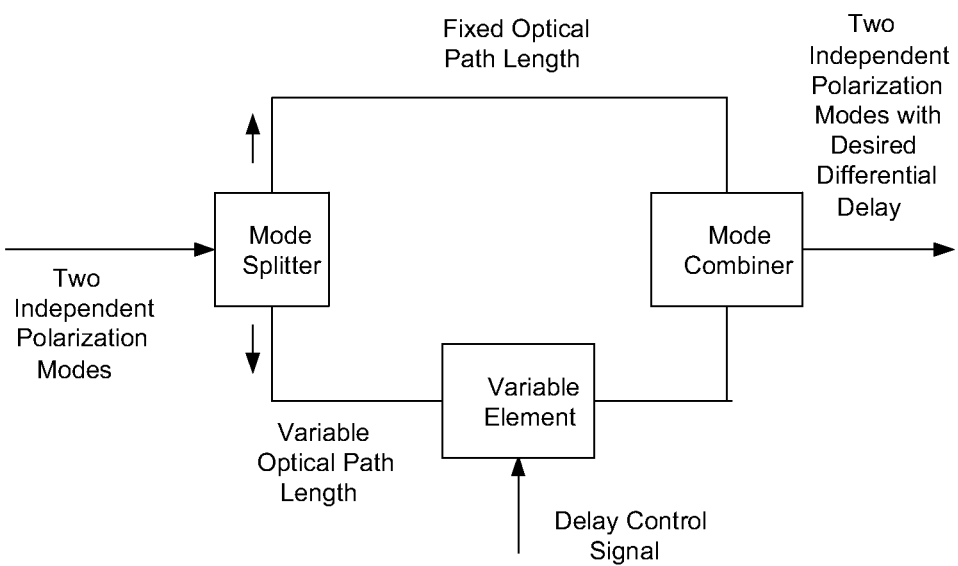

The variable delay element in one of the two optical paths may be implemented in various configurations. For example, the variable delay element may be a mechanical element. A mechanical implementation of the device in FIG. 11C may be constructed by first separating the radiation by polarization modes with a polarizing beam splitter, one polarization mode propagating through a fixed optical path while the other propagating through a variable optical path having a piezo-electric stretcher of polarization maintaining fibers, or a pair of collimators both facing a mechanically movable retroreflector in such a way that the light from one collimator is collected by the other through a trip to and from the retroreflector, or a pair collimators optically linked through double passing a rotatable optical plate and bouncing off a reflector.

Figure 12:
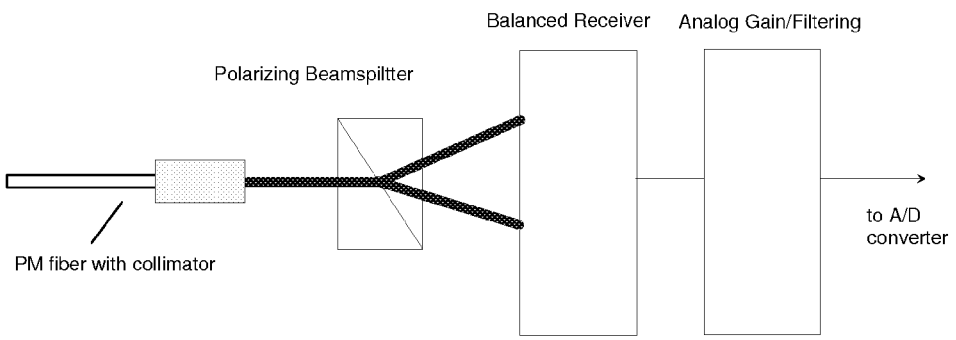
FIG. 12 shows an exemplary detection subsystem with a polarization beamsplitter.
Figure 13:
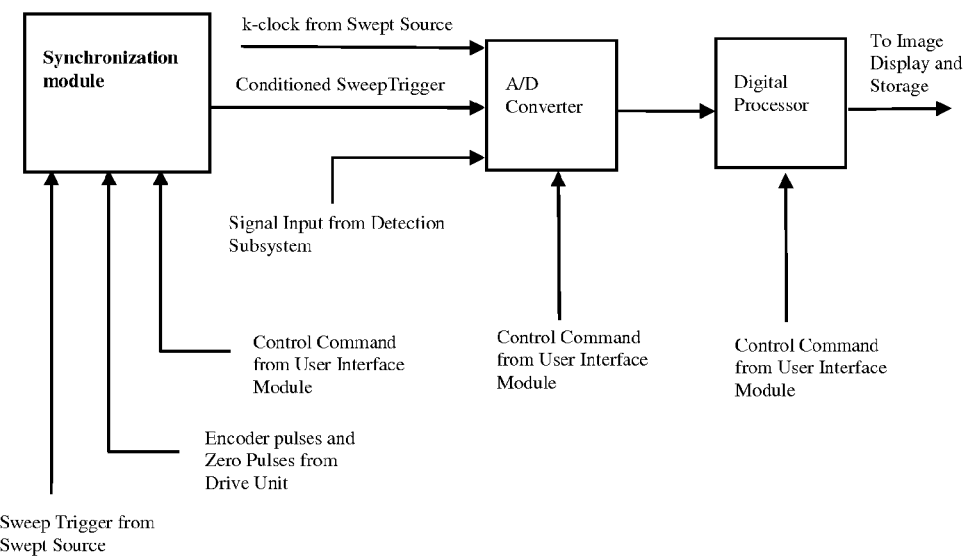
FIG. 13 shows an exemplary block-diagram of the Control and Signal Processing Subsystem.
Figure 14:
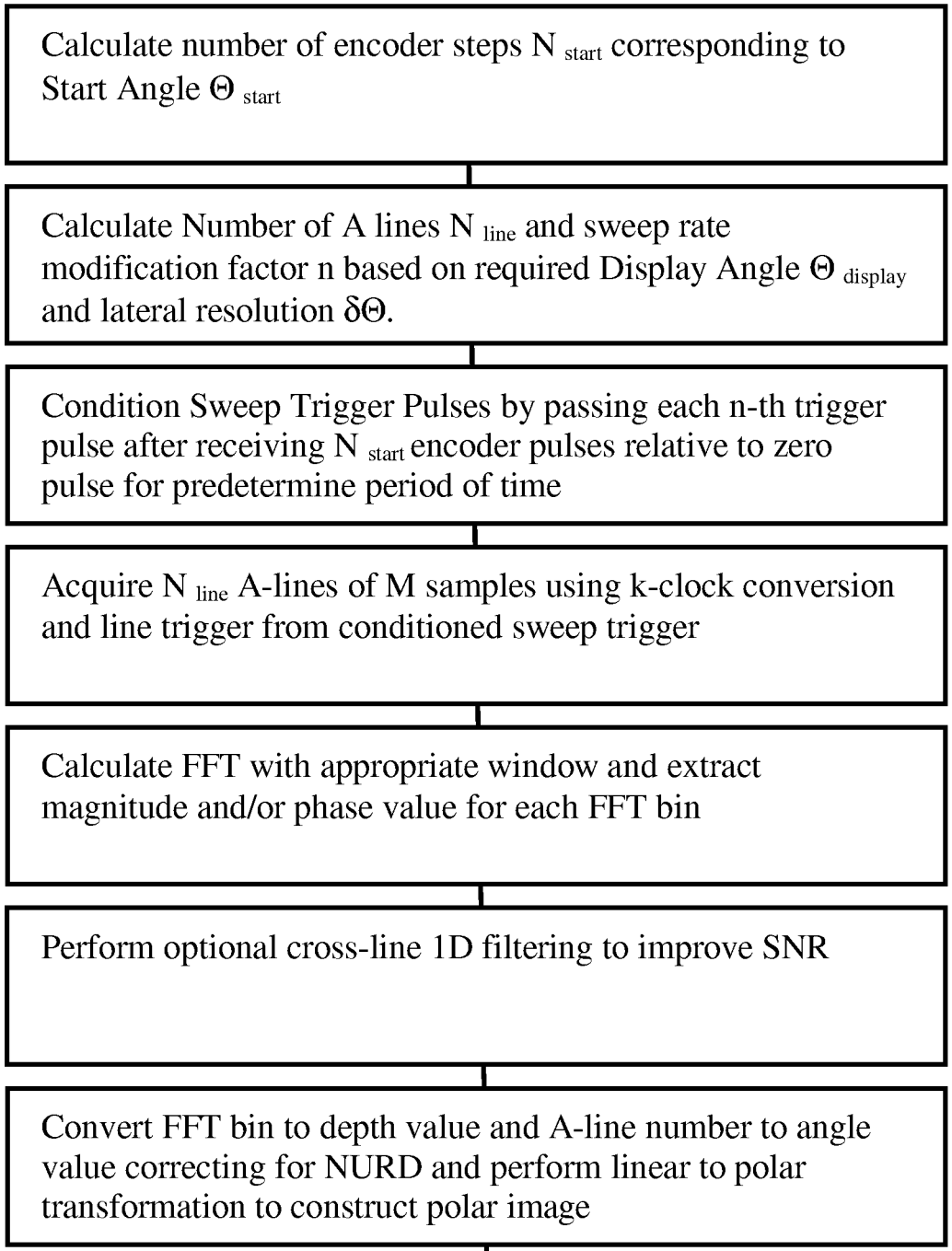
FIG. 14 shows an exemplary process flow for the Control and Signal Processing Subsystem.

In FIG. 1, the Detection Subsystem converts the backscattered light from the tissue into electrical signal upon mixing of propagation modes. The detection subsystem may be configured to include mechanism that mixes two propagation modes, mechanism that converts optical information into electrical signal, and electrical signal processing and filtering circuitry. An example of detection subsystem is shown in FIG. 12 with polarization beamsplitter as mode mixing element and the standard balanced optical receiver consisting of two optical detectors and subtraction, filtering, and amplification circuitry, followed by any additional standard electrical amplifiers and filters, e.g., anti-aliasing filters. In this example the polarizing beamsplitter can be oriented to minimize DC component of the signal at the output of the balanced detector to optimize sensitivity of OFDI. It is understood that any standard polarization beamsplitter and/or optical detectors can be used in the detection subsystem Controls and Signal Processing Subsystem in FIG. 1 synchronizes swept source wavelength tuning, Optical Rotary Shaft rotation within the Disposable Catheter and analog-to-digital (A/D) conversion, then digitizes the electrical signal provided by the Detection Subsystem and then performs Digital Fourier Transform (DFT) and other digital signal processing (DSP) steps known in the field of OFDI. FIGS. 13 and 14 show exemplary block-diagram and the operation flow chart of the Control and Signal Processing Subsystem, respectively.

Display Storage and User Interface Module in FIG. 1 is designed to store and display obtained images such as stand alone or embedded computer and monitor and also means to obtain user inputs such as keyboards, keypads, foot pad and alike.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications, and enhancements to the described examples and implementations and other implementations can be made based on what is disclosed.

What is claimed is what is described and illustrated, including:

1. A device for optically imaging a sample, comprising:
   a swept frequency light source that produces an optical probe beam and sweeps an optical frequency of the optical probe beam in time;
   a waveguide to receive and guide optical probe beam in a first propagation mode and a second propagation mode different from the first propagation mode;
   a disposable probe head unit removably coupled to the waveguide to receive the optical probe beam in first and second propagation modes and to reflect a first portion of the optical probe beam back to the waveguide in the first propagation mode and direct a second portion of the optical probe beam to a sample, the probe head collecting reflection of the second portion from the sample and exporting to the waveguide the reflection as a reflected second portion in the second propagation mode;
   a mode director that directs the optical probe beam from the swept frequency light source into the waveguide and to couple light of the reflected first portion and the reflected second portion out of the waveguide without changing respective propagation modes;
   a mode controller coupled in an optical path of the optical probe beam between the swept frequency light source and the mode director to control light in the first and second propagation modes;
   a differential delay controller in an optical path of both the reflected first portion and the reflected second portion from the mode director to control a relative delay between the reflected first portion and the reflected second portion; and
   an optical detector unit that receives the light from the differential delay controller and to produce an electrical signal containing imaging information of the sample.

2. The device as in claim 1, comprising:
   a detection module to receive the reflected first portion and the reflected second portion in the waveguide and to extract information of the sample carried by the reflected second portion.

* * * * *